United States Patent
Kajan et al.

(10) Patent No.: US 10,247,650 B2
(45) Date of Patent: Apr. 2, 2019

(54) PORTABLE ALCOHOL TESTER

(71) Applicant: VIRGINIA COMMONWEALTH UNIVERSITY, Richmond, VA (US)

(72) Inventors: Illya Kajan, Richmond, VA (US); David Saul, Richmond, VA (US); Boris Solomonov, Henrico, VA (US); Alex Ucci, Richmond, VA (US); Matthew Leccadito, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 144 days.

(21) Appl. No.: 15/463,064

(22) Filed: Mar. 20, 2017

(65) Prior Publication Data

US 2017/0269048 A1 Sep. 21, 2017

Related U.S. Application Data

(60) Provisional application No. 62/310,856, filed on Mar. 21, 2016.

(51) Int. Cl.
*G01N 7/16* (2006.01)
*G01N 33/14* (2006.01)

(52) U.S. Cl.
CPC .............. *G01N 7/16* (2013.01); *G01N 33/146* (2013.01)

(58) Field of Classification Search
CPC .............................. G01N 7/16; G01N 33/146
See application file for complete search history.

(56) References Cited

U.S. PATENT DOCUMENTS 5,159,898 A * 11/1992 Hartel ................. F02D 19/0605
123/1 A
2008/0314127 A1* 12/2008 Kinkade, Jr. ........ G01N 31/005
73/53.05

\* cited by examiner

*Primary Examiner* — Paul M. West
(74) *Attorney, Agent, or Firm* — W & C IP

(57) ABSTRACT

A portable electronic alcohol-testing device is provided that uses vaporization and sensitive pressure guages to approximate the alcohol content of a solution. The device may be used, for example, to determine the relative alcohol content of a mixed beverage.

6 Claims, 4 Drawing Sheets

100% Alcohol=40%ABV
(vodka)
50% Alcohol=20%ABV

PORTABLE ALCOHOL TESTER

CROSS REFERENCE TO RELATED APPLICATIONS

This application claims priority to U.S. Provisional Application 62/310,856 filed Mar. 21, 2016, herein incorporated by reference.

FIELD OF THE INVENTION

Embodiments of the invention provide a portable electronic alcohol-testing device that detects the relative alcohol content of a liquid, such as a mixed beverage.

BACKGROUND OF THE INVENTION

The presence of alcohol in collegiate social settings is a primary threat to the health and safety of over twenty million college students in the United States. Recent studies confirm at least fifty percent reported that regrettable actions were performed, memory of accountability of their actions were lost, police enforcement was involved, unprotected sex occurred, harm came to themselves or others and lastly, harm to themselves or others took place while driving under the influence of alcohol. These findings took place 12 months prior to being surveyed. If current trends continue, 50% of college age women will be sexually assaulted during their university career; 87% of those assaults involving alcohol as an underlying factor. Students often over-serve themselves at parties because they are unaware of the amount of alcohol in a given beverage. A common "punch" recipe creates a drink which typically contains 27% alcohol-by-volume (ABV), five times as much as beer and twice as much as wine. One serving of this mixture contains 4.32 ounces of pure, 100% alcohol, the equivalent of 7 shots. Currently, there are no technologies on the market to help people understand the alcohol content of a beverage before they consume it. Thus, there is a need for an affordable, quick-response, multi-use technology to determine the alcohol content of unmarked party beverages.

SUMMARY OF THE INVENTION

The alcohol tester, according to embodiments of the invention, is a portable device comprised of an enclosure; a sampling reservoir at one end of said enclosure; at least one pressure relief valve for releasing pressure from within the enclosure; and a heating element, at least one pressure sensor, and a control logic board contained within the enclosure, wherein the heating element heats the liquid sample, at least one pressure sensor measures pressure inside the enclosure at a first temperature and a second temperature, and the control logic board receives a pressure reading from the pressure sensor and computes the alcohol content of a liquid sample received in the sampling reservoir.

In some embodiments, the enclosure has a tubular shape. In additional embodiments, the portable device further comprises a battery, a visual indicator on the outside of said enclosure, and/or a manual pressing element at an end of said enclosure opposite to said sampling reservoir, wherein said manual pressing element is operably connected to said sampling reservoir. In some embodiments, the at least one pressure relief valve is a controlled pressure relief valve.

Another aspect of the invention provides A method for measuring the alcohol content in a liquid, comprising the steps of gathering a sample of the liquid into a sampling reservoir, heating the sample with a heating element to a first temperature, releasing evaporated gas through a pressure relief valve, using the pressure sensor to obtain a baseline pressure reading, heating the sample with the heating element to a second temperature, using the pressure sensor to obtain a pressure reading after the sample is heated to the second temperature, and calculating the alcohol content based on a pressure differential between the pressure reading at the second temperature and the baseline pressure reading. In some embodiments, the method further comprises the step of providing the calculated alcohol content through a visual indicator on the outside of said enclosure. In some embodiments, the first temperature is 60° C. and the second temperature is 80° C.

Additional features and advantages of the invention will be set forth in the description below, and in part will be apparent from the description, or may be learned by practice of the invention. The advantages of the invention can be realized and attained by the exemplary structure particularly pointed out in the written description and claims hereof as well as the appended drawings.

DETAILED DESCRIPTION

Embodiments of the invention provide a portable device for measuring alcohol content in a liquid. The device is preferably manufactured with dimensions allowing for its portability and use in testing beverages. In some embodiments, the device approximates the size of an electronic cigarette. A device as described herein has applications in various industries such as home and craft brewing, scientific instruments, as well as applications within law enforcement by allowing alcohol-related evidence to be collected and tested in the field. Further, a device of the invention could be used in social settings to determine the alcohol content of unknown mixed beverages. It is also contemplated that the device is used to test for the presence of other chemicals or drugs that are present in a solution.

Figure 1:
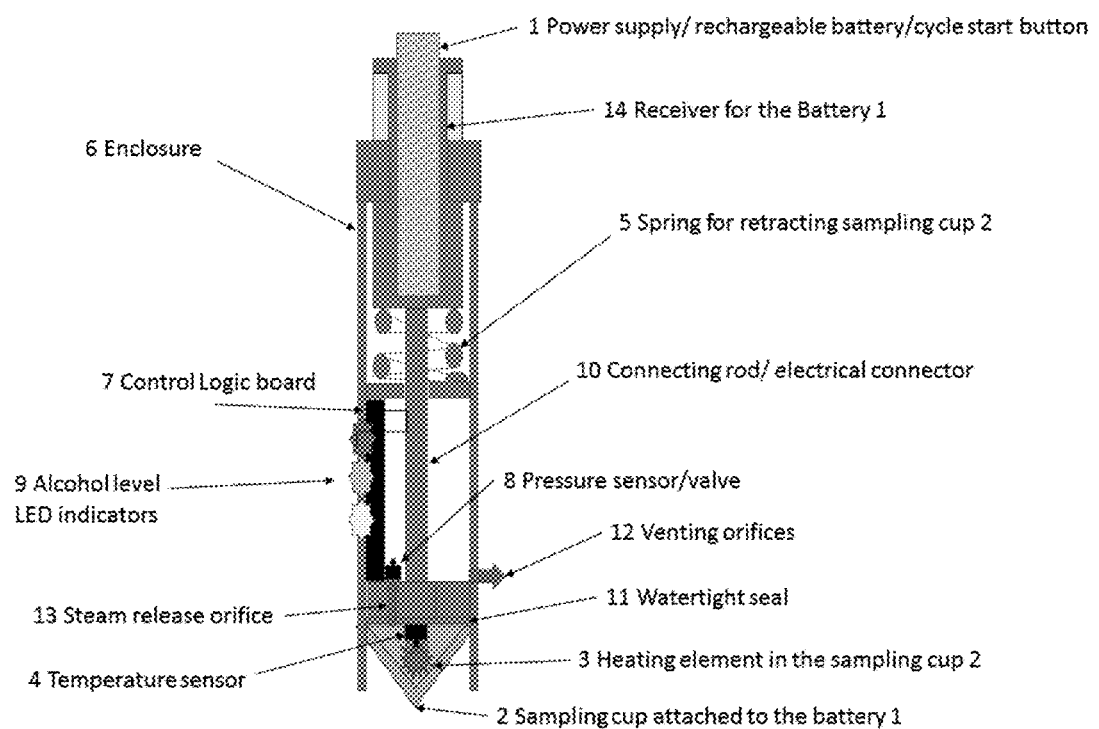
FIG. 1. An exemplary embodiment of the alcohol tester.

FIG. 1 illustrates an exemplary embodiment of an alcohol tester of the invention. As shown in FIG. 1, the portable device comprises an enclosure 6; a sampling reservoir 2 at one end of said enclosure 6; at least one pressure relief valve 12 on a side of the enclosure; a heating element 3, at least one pressure sensor 8, and a control logic board 7 contained within the enclosure.

The enclosure 6 may be configured in a variety of shapes, for example, rectangular, triangular, or tubular. The interior space of the enclosure 6 may be subdivided to provide separate spaces for each of the components of the device. The enclosure 6 may be formed of plastic, fiberglass, ceramic, metal, or any other appropriate material.

The sampling reservoir 2 is provided at one end of the enclosure 6 and is configured to intake a liquid sample of about 0.2 mL to about 1 mL, about 0.4 mL to about 0.6 mL, and preferably about 0.5 mL. A watertight seal 11 may also be provided on a least one side of the sampling reservoir 2. The device may further comprise a manual pressing element 1 at an end of said enclosure opposite to said sampling reservoir 2, wherein said manual pressing element is operably connected to said sampling reservoir 2, e.g. via a connecting rod 10. Thus, when a user presses the element 1, the sampling reservoir 2 is opened to collect the sample. The sampling reservoir 2 can be closed by pressing the element 1 again. A spring 5 may be provided within the enclosure to allow for the retraction/closing of the sampling reservoir 2. In some embodiments, the sampling reservoir 2 contains a sensor that allows for the sampling reservoir 2 to automatically open when in contact with a liquid.

The manual pressing element 1 may comprise a battery inserted into a receiver 14 formed from the enclosure 6. In some embodiments, the battery is rechargeable. In some embodiments, the battery is removable so that when exhausted, a fresh battery is substituted.

At least one heating element 3 and temperature sensor 4 are provided within the enclosure 6, e.g. within the sampling reservoir 2. Heating elements, such as those which convert electricity into heat through resistive or joule heating, e.g. as provided in electronic cigarettes, are known in the art. Temperature sensors, such as thermistors, are also well known in the art. A steam release orifice 13 and at least one pressure release valve 12 are provided to relieve pressure within the enclosure 6.

A sensitive pressure sensor 8 detects pressure changes within the enclosure 8 before and after a sample has been heated. Suitable pressure sensors are known in the art and include, but are not limited to Microelectomechanical Systems (MEMS) based differential barometric pressure sensor, which may include a MEMS temperature sensor in the same package, or include an external temperature sensor embedded on the same Printed Circuit Board (PCB).

A control logic board 7, e.g. a microcontroller, is configured to receive a pressure reading from the pressure sensor 8 and for carrying out the method of calculating, e.g. through back extrapolation, the alcohol content of a liquid sample received in the sampling reservoir.

Figure 2:
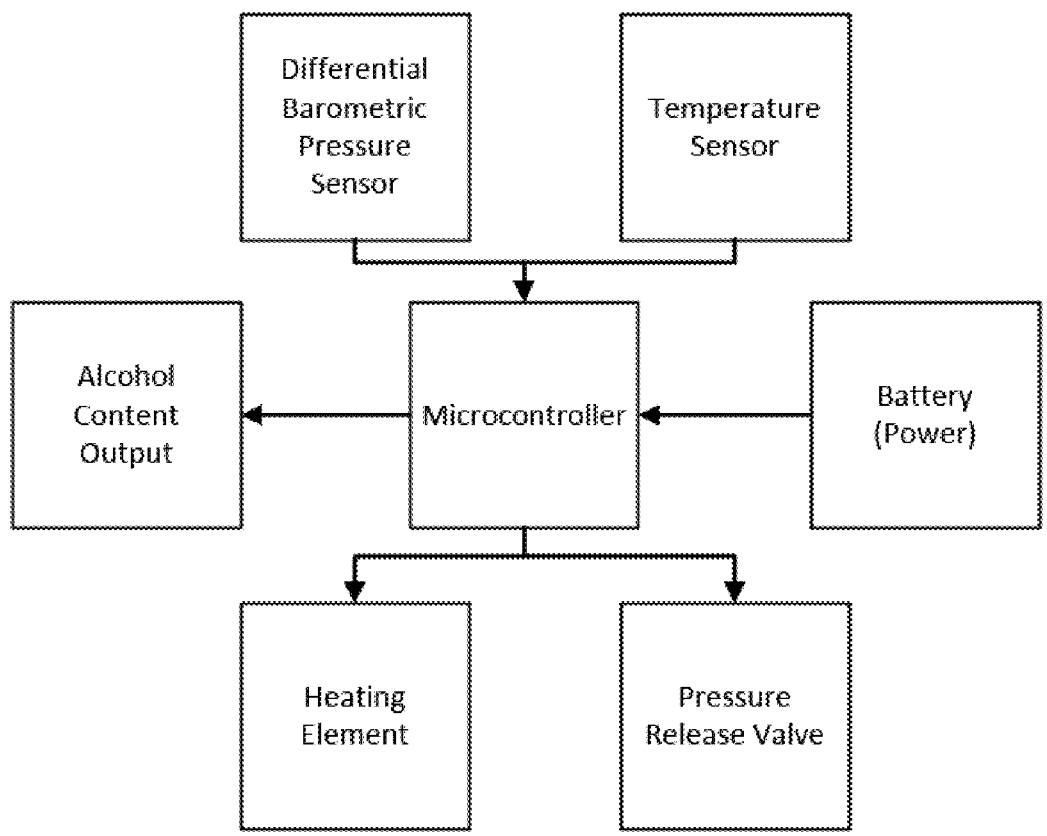
FIG. 2. Lay out of the logic board.

The layout of the logic board is depicted in FIG. 2. The microcontroller may be battery operated, while coordinating all of the device tasks. The microcontroller can monitor the temperature, operate the heating element, and the pressure release valve, gauge the barometric pressure, and provide the alcohol output.

Once the alcohol content of a liquid has been determined, the device provides a visual, audible, or tactile, e.g. a vibration, indication of the content. For example, a digital numerical display is used to indicate the calculated alcohol content. In other embodiments, one or more light indicators 9 are provided.

Figure 3:
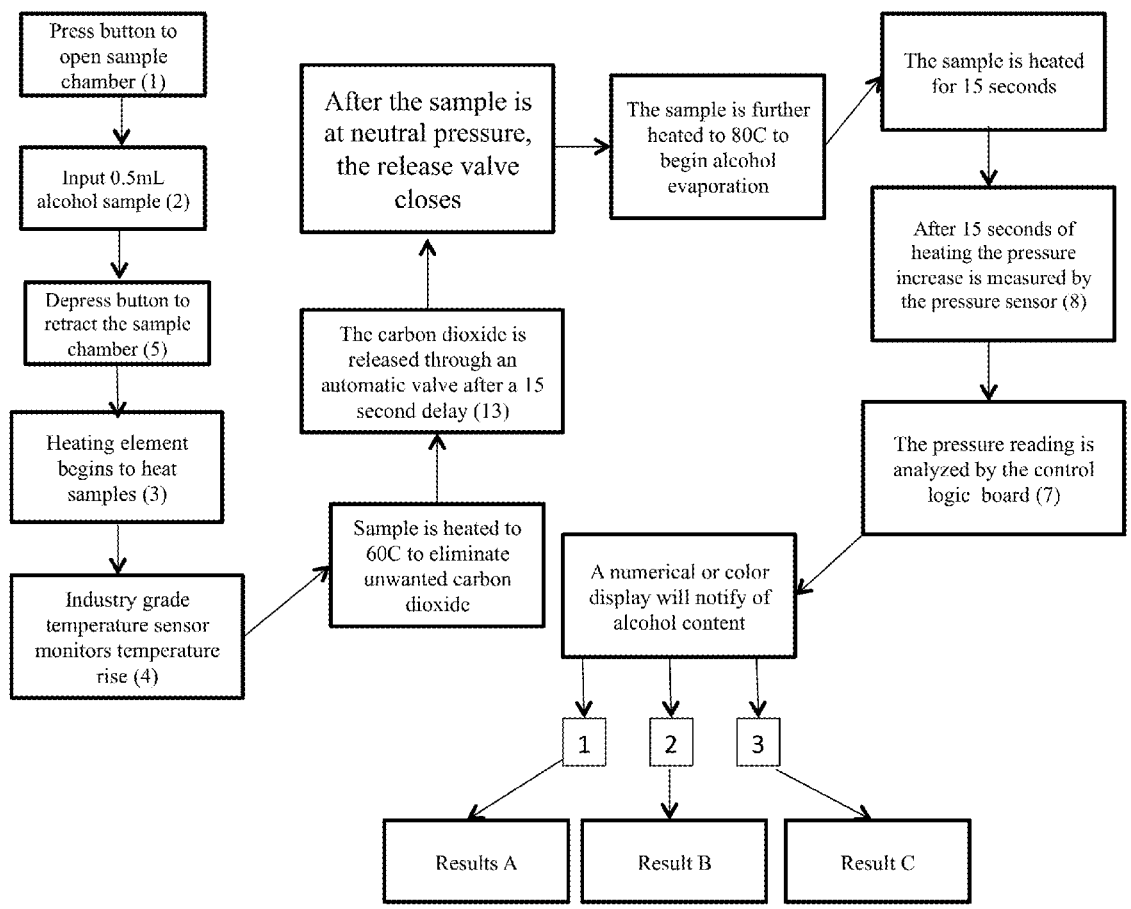
FIG. 3. Flow chart illustrating an exemplary operation of the alcohol tester.

A flow chart illustrating an exemplary operation of the alcohol tester is shown in FIG. 3. The method begins by the collection of a liquid sample as discussed herein. Once in the reservoir, the test can include two stages. If the sample is carbonated, then in the first stage of the process, the sample will be heated to about 60° C. to ensure quick elimination of unwanted carbon dioxide (thus eliminating false readings), which will be released through a small pressure relief valve. After about 15 seconds at 60° C., all of the carbon dioxide will be eliminated from the sample, and the sample will be at neutral pressure. At this stage, the relief valve will be closed and a baseline pressure reading taken. Then, the sample chamber will be heated to about 80° C. to begin alcohol evaporation from the sample. This step will proceed for about 15-30 seconds, at the end of which the pressure change within the chamber will be measured. After a pressure change is measured by the device, relative alcohol content will be calculated, for example through back extrapolation, and a light sensor, or a numerical display will be illuminated to alert the user of the relative alcohol content, e.g. Result A-Low Content, Result B-Medium Content, and Result C-High Content. Therefore, within 30 seconds, the tester allows the user to determine the alcohol content of the mixed beverage, relative to the pressure increase. The pressure rise within the chamber is directly correlated to the alcohol content of the unknown beverage. After the test is complete the user will be able to either pour the taken sample back into the beverage, or discard it.

The time and temperature required for each heating step may be varied in additional embodiments of the invention. For example, the temperature may range from about 50° C. to about 100° C. and the heating step may last for about 10 seconds up to about 1 minute.

Figure 4:
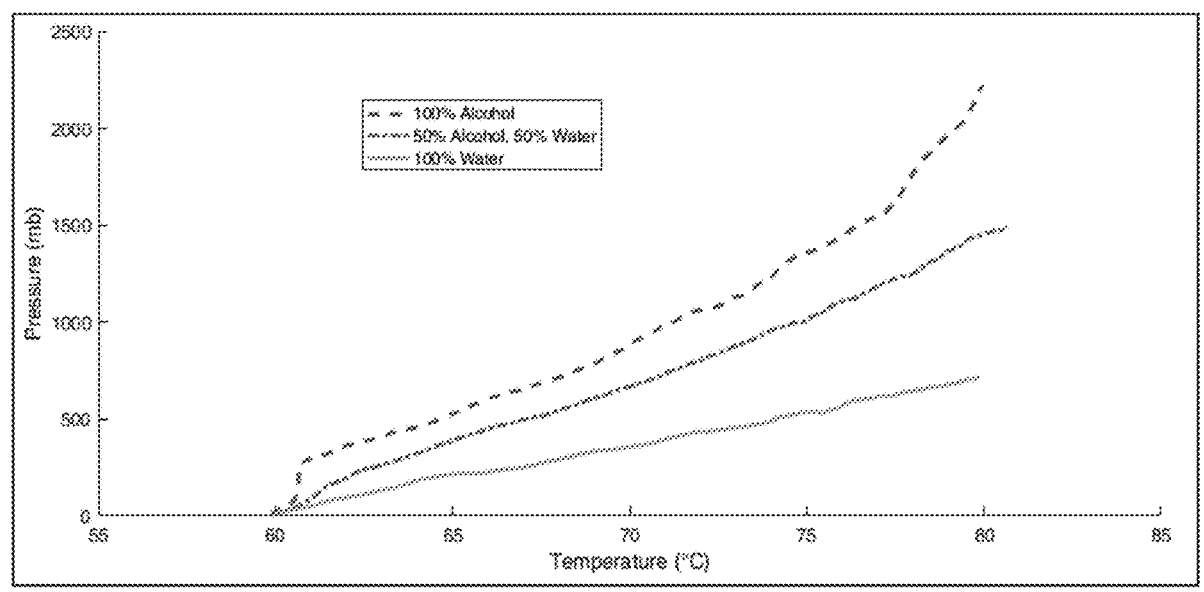
FIG. 4. Measurement of the alcohol content of a solution.

As shown in FIG. 4, a device performing the aforementioned steps is able to accurately measure the relative alcohol content of a solution. Testing was conducted with controlled mixtures of alcohol in order to elicit at pressure gradient. A negative control of 100% water was used to establish a baseline pressure reading. A positive control of (40% alcohol by volume) vodka was used to establish a second baseline reading. The experiment group was a mixture of water and vodka that was diluted to 20% alcohol by volume. The experiment demonstrated that it is possible to establish the alcohol content of a mixture based on change in relative pressure due to a rise in temperature.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method for measuring the alcohol content in a liquid, comprising the steps of
   gathering a sample of the liquid into a sampling reservoir,
   heating the sample with a heating element to a first temperature of 60° C.-70° C.,
   releasing evaporated gas through a pressure relief valve,
   using a pressure sensor to obtain a baseline pressure reading,
   heating the sample with the heating element to a second temperature different from said first temperature,
   using the pressure sensor to obtain a pressure reading after the sample is heated to the second temperature, and
   calculating the alcohol content based on a pressure differential between the pressure reading at the second temperature and the baseline pressure reading.

2. The method of claim 1, further comprising the step of providing the calculated alcohol content through a visual indicator.

3. The method of claim 1, wherein the second temperature is 80° C.-90° C.

4. A method for measuring the alcohol content in a liquid, comprising the steps of
   gathering a sample of the liquid into a sampling reservoir,
   heating the sample with a heating element to a first temperature,
   releasing evaporated gas through a pressure relief valve,
   using a pressure sensor to obtain a baseline pressure reading,
   heating the sample with the heating element to a second temperature different from said first temperature, wherein the second temperature is 80° C.-90° C.,
   using the pressure sensor to obtain a pressure reading after the sample is heated to the second temperature, and
   calculating the alcohol content based on a pressure differential between the pressure reading at the second temperature and the baseline pressure reading.

5. The method of claim 4, further comprising the step of providing the calculated alcohol content through a visual indicator.

6. The method of claim 4 wherein the first temperature is 60° C.-70° C.

* * * * *